United States Patent
Conti et al.

(10) Patent No.: US 9,040,575 B2
(45) Date of Patent: May 26, 2015

(54) COMBINATION FOR THE TREATMENT OF OSTEOARTHRITIS

(71) Applicant: PROFESSIONAL DIETETICS, S.R.L., Milan (IT)

(72) Inventors: Franco Conti, Milan (IT); Francesco Saverio Dioguardi, Milan (IT)

(73) Assignee: PROFESSIONAL DIETETICS, S.R.L., Milan (IT)

( * ) Notice: Subject to any disclaimer, the term of this patent is extended or adjusted under 35 U.S.C. 154(b) by 21 days.

(21) Appl. No.: 13/947,538

(22) Filed: Jul. 22, 2013

(65) Prior Publication Data

US 2013/0310437 A1 Nov. 21, 2013

Related U.S. Application Data

(63) Continuation of application No. 13/517,307, filed as application No. PCT/EP2010/069451 on Dec. 13, 2010, now abandoned.

(30) Foreign Application Priority Data

Dec. 21, 2009 (IT) .................. MI2009A2256

(51) Int. Cl.
| | |
|---|---|
| *A01N 43/36* | (2006.01) |
| *A61K 31/40* | (2006.01) |
| *A61K 31/401* | (2006.01) |
| *A61K 9/00* | (2006.01) |
| *A61K 31/198* | (2006.01) |
| *A61K 31/717* | (2006.01) |
| *A61K 31/728* | (2006.01) |
| *A61K 31/79* | (2006.01) |
| *A61K 45/06* | (2006.01) |
| *A61K 47/36* | (2006.01) |
| *A61L 27/54* | (2006.01) |

(52) U.S. Cl.
CPC ............ *A61K 31/401* (2013.01); *A61K 9/0019* (2013.01); *A61K 31/198* (2013.01); *A61K 31/717* (2013.01); *A61K 31/728* (2013.01); *A61K 31/79* (2013.01); *A61K 45/06* (2013.01); *A61K 47/36* (2013.01); *A61L 27/54* (2013.01); *A61L 2300/40* (2013.01)

(58) Field of Classification Search
None
See application file for complete search history.

(56) References Cited

U.S. PATENT DOCUMENTS

| | | | |
|---|---|---|---|
| 2005/0053673 A1 | 3/2005 | Netke et al. | |
| 2009/0197807 A1* | 8/2009 | Callegaro et al. | ............... 514/12 |

FOREIGN PATENT DOCUMENTS

| | | |
|---|---|---|
| EP | 1 010 427 A1 | 6/2000 |
| EP | 1 161 945 A2 | 12/2001 |
| EP | 1161945 A2 * | 12/2001 |
| WO | 2006/067608 A1 | 6/2006 |
| WO | WO 2006067608 A1 * | 6/2006 |
| WO | 2007/048523 A1 | 5/2007 |
| WO | 2007/048524 A2 | 5/2007 |

OTHER PUBLICATIONS

Park et al, Arthritis Research & Therapy 2007, 9:R8.*
Poole et al, Ann. Rheum. Dis2002;61(Suppl II):ii78-ii81.*
Yosipovitch, Z.H. and Glimcher, M.J., "Articular Chondrocalcinosis, Hydroxypatite Deposition Disease in Adult Mature Rabbits," The Journal of Bone and Joint Surgery, Vo. 54a, No. 4, Jun. 1972, pp. 841-853, XP009136880.

* cited by examiner

*Primary Examiner* — Wu-Cheng Winston Shen
*Assistant Examiner* — Jean Cornet
(74) *Attorney, Agent, or Firm* — Silvia Salvadori, P.C.

(57) ABSTRACT

The present invention relates to the use of a combination of glycine, proline, and optionally a natural or synthetic viscosity-controlling polymer, and/or lysine and/or leucine, to prepare a composition for the treatment of osteoarthritis.

7 Claims, No Drawings

COMBINATION FOR THE TREATMENT OF OSTEOARTHRITIS

This application is a continuation of U.S. application Ser. No. 13/517,307, filed on Aug. 1, 2012, which is a U.S. National Stage of PCT/EP2010/069451 filed on Dec. 13, 2010, which claims priority to and the benefit of Italian Application No. MI2009A002256 filed on Dec. 21, 2009, the contents of which are incorporated herein by reference in their entirety.

The present invention relates to a combination of glycine, proline, and optionally a natural or synthetic viscosity-controlling polymer, and/or lysine and/or leucine, for the treatment of osteoarthritis, in particular for patellofemoral or femorotibial osteoarthritis of the knee, osteoarthritis of the hip and osteoarthritis of the shoulder.

TECHNICAL BACKGROUND

Osteoarthritis is the most common joint disease among the rheumatic disorders affecting the Western world. It is a chronic degenerative joint disease which may be diffuse or localised, affecting the cartilage of the diarthrodial joints, where the normal metabolic process of the chondrocytes is impaired, leading to softening, fibrillation, ulceration and subsequent sclerosis of the subchondral bone, and in the final stages to new bone formation and subchondral cysts.

Osteoarthritis, which mainly affects women, most frequently involves the patellofemoral joint, the femorotibial joint, the hip and the shoulder. Osteoarthritis of the knee, or gonarthritis, is particularly frequent and disabling. The clinical picture is initially dominated by characteristically mechanical pain at the anterior or anteromedial site, which is attenuated by rest. After lengthy inactivity, for example in the mornings or after sitting for a long time, painful post-inactivity spasms may be experienced. However, they are shortlived, and attenuated by walking. Pain may be triggered by using stairs, especially walking downstairs, squatting, especially in the case of patellofemoral osteoarthritis, or lengthy use of vehicle pedals. Initially there may also be pain in the periarticular areas, and modest effusion. The pain may later affect the whole joint, become nocturnal, and be accompanied by frequent joint effusions. Functional impairment only appears at a late stage, despite the presence of a considerable valgus or varus malalignment.

Until a few years ago the main therapeutic objective of the treatment of knee osteoarthritis was controlling the symptoms (pain and functional limitation), traditionally achieved with NSAIDs (non-steroidal anti-inflammatory drugs) and other painkillers.

The ideal treatment of knee osteoarthritis requires a combination of pharmacological and other treatments, which must be tailored to the patient's requirements on the basis of local risk factors (obesity, mechanical factors, physical activity), general risk factors (age, comorbidity, multiple drug therapy), pain intensity levels and degree of disability, signs of inflammation (effusion), location and degree of structural damage.

Non-pharmacological treatment of knee osteoarthritis should include rehabilitation programmes, physical exercise, the use of aids (walking sticks, insoles or knee braces) and weight loss, where necessary.

The first-line medicament for the treatment of pain in knee osteoarthritis is paracetamol, which is used at doses lower than or equal to 3 gm/day in addition to other osteoarthritis drugs.

Topical applications of NSAIDs or capsaicin can be a useful treatment if used for short periods, especially for patients who refuse or are unable to take oral medicaments.

NSAIDs are considered for patients who fail to respond to paracetamol and patients at gastrointestinal risk; in that case, conventional COXIBs or NSAIDs associated with proton pump inhibitors are used.

Opioid analgesics represent useful alternatives in patients for whom NSAIDs or COXIBs are contraindicated because they are ineffective or poorly tolerated.

Other drugs used are those which, when administered by the oral or intra-articular route, reduce the clinical symptoms at varying rates, by different methods from analgesics or NSAIDs. This group consists of two different categories: slow-acting symptomatic medicaments for osteoarthritis, and medicaments able to modify the progress of osteoarthritis. Glucosamine sulphate, chondroitin sulphate, soya and avocado extracts, diacerein, hyaluronic acid and S-adenosylmethionine belong to the first group. These medicaments have a direct action on the chondrocytes and synoviocytes and consequently have beneficial effects on the cartilage structure. Their efficacy against the symptoms starts slowly (1-2 weeks) but lasts for a long time: up to two months after discontinuance of the treatment.

Intra-articular injection of cortisones with a long-lasting action is indicated for acute joint pain, especially if it is associated with intra-articular effusions.

Research currently focuses on molecules with specific effects on the pathogenetic mechanisms of osteoarthritis, modifying both the symptoms and the joint structure to counteract the progress of the disease.

International patent application PCT/EP2006/009966 describes wound-healing pharmaceutical compositions comprising a combination of glycine, lysine, leucine and proline and sodium hyaluronan, which is particularly effective in facilitating the cell renewal process that forms the basis of rapid wound-healing, promoting connective tissue reconstruction and consequent regeneration of the epithelial cells.

DESCRIPTION OF THE INVENTION

It has now been found that the use of intra-articular compositions comprising glycine, proline, and optionally a natural or synthetic viscosity-controlling polymer, lysine and/or leucine, is effective in the treatment of osteoarthritis, especially as regards the aspect of pain management.

The compositions according to the invention have a significant effect on pain reduction and improvement in the joint function, and consequently on the patient's quality of life. This effect is long-lasting, even after the treatment is discontinued (up to two months).

The use of the compositions according to the invention therefore provides a useful treatment for osteoarthritis, especially in pain management, offering fast, effective pain reduction.

The present invention therefore relates to a combination comprising:
 a) glycine,
 b) proline,
 and optionally
 c) a natural or synthetic viscosity-controlling polymer, and/or
 d) lysine, and/or
 e) leucine,
 for intra-articular administration for the treatment of osteoarthritis, in particular knee osteoarthritis.

According to the invention, the natural or synthetic viscosity-controlling polymer is selected from hyaluronic acid or a salt thereof, polyvinylpyrrolidone, and cellulose derivatives.

According to a preferred aspect, the natural or synthetic viscosity-controlling polymer is hyaluronic acid or a salt thereof.

According to the invention, the aminoacids are present in the L form.

According to a preferred aspect, the intra-articular compositions according to the invention will contain the various active constituents in the following composition ranges by weight:
- a) 25 to 500 mg of glycine,
- b) 40 to 300 mg of proline, and optionally
- c) 5 to 50 mg of hyaluronic acid or a salt thereof, and/or
- d) 5 to 100 mg of lysine, and/or
- e) 5 to 50 mg of leucine.

The compositions according to the invention are formulated suitably for intra-articular administration in the form of reconstitutable powders, solutions and the like, and will be prepared according to conventional methods well known in pharmaceutical technology, such as those described in Remington's Pharmaceutical Handbook, Mack Publishing Co., N.Y., USA, using excipients suitable for their final use.

Pharmacological Tests

The purpose of the trial was to evaluate the therapeutic efficacy of intra-articular administration of a composition according to the invention in patients suffering from primary osteoarthritis of the knee by assessing the thickness of the cartilage, the intensity of pain and the patients' quality of life before and after treatment.

The composition according to the invention used for the trial consisted of 2 bottles: bottle A, containing sodium hyaluronan in aqueous solution; and bottle B, containing a freeze-dried powder based on glycine (182 mg), L-proline (150 mg), L-lysine (35 mg) and L-leucine (21 mg). Before administration, the product must be reconstituted (the freeze-dried powder in bottle B is dissolved in the solution contained in bottle A) to provide a transparent solution containing no particulate matter.

The area to be treated was disinfected, and then anaesthetised with an anaesthetic cream to be applied 30 minutes before the operation. The infiltrations were repeated once a week for 5 weeks.

No overdoses or interactions with other medicaments are known. Rarely, local reactions due to hypersensitisation may occur, manifested by oedema, a sensation of warmth and/or itching.

11 patients suffering from knee osteoarthritis (7 men aged between 50 and 80 years and 9 women aged between 51 and 72 years) were examined. The staging of the degree of osteoarthritis was performed according to the Kellgren and Lawrence score (Kellgren J H, Lawrence J S. Radiological assessment of osteo-arthrosis. *Ann Rhem Dis* 1957; 16: 494-502).

The inclusion criteria were:

1) Diagnosis of knee osteoarthritis according to the ACR (American College of Rheumatology) diagnostic criteria
knee pain associated with at least three of the following criteria:
- a—age over 50 years
- b—stiffness after resting for less than thirty minutes
- c—creaking
- d—bone pain
- e—enlargement of bone contour, not warm on palpation 2) Radiological stage of disease between I and II on the Kellgren and Lawrence scale.

I: doubtful reduction in joint space and possible formation of osteophytes,

II: well-defined osteophytes, and possible reduction in joint space,

III: multiple osteophytes and well-defined reduction in joint space, sclerosis and possible deformity of bone contour, IV: large osteophytes, marked reduction in joint space, severe sclerosis and well-defined deformity of bone contour.

The whole population examined presented radiological stage II of the disease apart from one woman, with stage I.

On entry to the trial, and after 3 and 6 months, a case history was taken with collection of personal and anthropometric data (height, weight, body mass index (BMI), blood pressure and heart rate), and the following parameters were evaluated:

Intensity of pain on a visual analogue scale (VAS), expressed in millimeters from 0 (normal) to 100 (maximum intensity of pain), performed by both the doctor and the patient;

Severity of disease using the Womac (Western Ontario and McMaster Universities) Osteoarthritis Index questionnaire, a scale of self-assessment of knee osteoarthritis, consisting of 24 items used to monitor the progress of the disorder and determine the efficacy of the treatment.

Thickness of knee joint cartilage in the central, medial and lateral compartment by means of an ultrasound scan (performed with a Philips Envisor 250 ultrasound system with multifrequency linear probe from 5 to 13 MHz).

Results

The composition according to the invention was well tolerated, with no local or systemic allergic reactions. The results of the clinical evaluation are set out in Tables I and II.

The data relating to evaluation of pain intensity and the severity of the disease are set out in Table I below.

a) Pain Intensity Assessment

The mean pain value (VAS) evaluated by patients at the beginning of the trial was 58.03 ($\pm$8.31); after three months, the mean value was 28.07 ($\pm$8.55), a percentage decrease of 58% ($p<0.05$); and after six months the mean value had fallen to 16.20 ($\pm$9.28) ($p<0.05$). The mean pain value (VAS) evaluated by the doctors at the beginning of the trial was 56.18 ($\pm$9.66); after three months, the mean value was 22.03 ($\pm$7.32), a percentage decrease of 54% ($p<: 0.05$); after six months the mean value had fallen still further, to 9.11 mm ($\pm$6.97), a percentage decrease of 71% compared with baseline ($p<0.05$).

b) Assessment of Severity of Disease

At the beginning of the trial the mean WOMAC value was 55.03 ($\pm$27.04); after three months the mean value had fallen to 24.00 ($\pm$25.44), a percentage decrease of 65% ($p<0.001$); and after six months the mean value had further decreased to 11.99 mm ($\pm$10.86), a percentage decrease of 83% compared with baseline ($p<0.001$).

TABLE I

Clinical evaluation of patients examined at the beginning of the trial (baseline), and 3 and 6 months after the infiltration treatment
CLINICAL EVALUATION

|  | baseline | 3 months comparison vs. baseline | 6 months comparison vs. baseline |
| --- | --- | --- | --- |
| patient VAS mean (SE) (range) | 58.03 ($\pm$ 8.31) (29-97) | 28.07 ($\pm$ 8.55) (6-63) $p < 0.05*$ | 16.20 ($\pm$ 9.28) (4-67) $p < 0.05*$ |

TABLE I-continued

Clinical evaluation of patients examined at the beginning of
the trial (baseline), and 3 and 6 months after the infiltration treatment
CLINICAL EVALUATION

|  | baseline | 3 months comparison vs. baseline | 6 months comparison vs. baseline |
|---|---|---|---|
| doctor VAS mean (SE) (range) (range) | 56.18 (± 9.66) (15-88) | 22.03 (± 7.32) (2-45) $p < 0.05$* | 9.11 (± 6.97) (3-42) $p < 0.05$* |
| WOMAC mean ± SD (range) | 55.03 ± 27.04 (18-89) | 24.00 ± 25.44 (4-68) $p < 0.001°$ | 11.99 ± 10.86 (4-31) $p < 0.001°$ |

*Wilcoxon test for paired data: t-test for paired data

The data relating to the percentage decreases in the clinical evaluations of the patients examined 3 and 6 months after the infiltration treatment are set out in Table II below.

TABLE II

Clinical evaluation of percentage decreases in clinical
evaluations 3 and 6 months after infiltration treatment
CLINICAL EVALUATION

|  | % decreases after 3 months | % decreases after 6 months |
|---|---|---|
| patient VAS mean ± SD (range) | 58 ± 27 (11-93) | 75 ± 22 (43-97) |
| doctor VAS mean ± SD (range) | 54 ± 16 (40-84) | 71 ± 27 (42-91) |
| WOMAC mean ± SD (range) | 65 ± 29 (13-92) | 83 ± 11 (65-93) | c) Thickness of Joint Cartilage

The ultrasound evaluation of the cartilage (presented in Table III) shows that the mean thickness of the medial cartilage at baseline was 0.13 mm (±0.07); after 3 months that thickness had increased to 0.14 mm (±0.08), a percentage increase of 6.5% (p=n/s); after six months it has further increased to 0.15 mm (±0.08), a percentage increase of 14.1% compared with baseline (p<0.05).

The mean thickness of the lateral cartilage at baseline was 0.18 (±0.06) mm; after 3 months it had increased to 0.19 (±0.07) mm, a percentage growth of 2.9% (p=n/s); after six months the mean value showed a statistically significant increase compared with baseline.

The mean thickness of the central cartilage after three months (0.29 mm±0.07) was not significant, whereas after six months (0.31±0.11 mm) there was a statistically significant increase compared with the baseline value.

TABLE III

Mean thickness of joint cartilage at the beginning of the
trial (baseline), and 3 and 6 months after infiltration treatment
THICKNESS OF JOINT CARTILAGE

|  | baseline | 3 months comparison vs. baseline | 6 months comparison vs. baseline |
|---|---|---|---|
| MEDIAL [mm] mean ± SD (range) | 0.13 ± 0.07 (0.09-0.25) | 0.14 ± 0.08 (0.08-0.26) p n.s. | 0.15 ± 0.08 (0.10-0.27) $p < 0.05$ |
| LATERAL [mm] mean ± SD (range) | 0.18 ± 0.06 (0.07-0.31) | 0.19 ± 0.07 (0.10-0.32) p n.s. | 0.21 ± 0.09 (0.10-0.32) $p < 0.05$ |
| CENTRAL [mm] mean ± SD (range) | 0.28 ± 0.05 (0.11-0.43) | 0.29 ± 0.07 (0.14-0.44) p n.s. | 0.31 ± 0.11 (0.14-0.45) $p < 0.05$ |

Analysis of the results set out above demonstrates a definite improvement in clinical symptoms after administration of the composition according to the invention. Said improvement, which was present after only 3 months, was maintained after 6 months, when a further benefit on the osteoarticular symptoms was observed. The VAS pain values after 3 and 6 months had significantly declined compared with baseline, demonstrating that the medicament does not merely increase the viscoelasticity of the synovial fluid, but also has a favourable effect on the pain symptom, and consequently on the patient's quality of life.

The invention claimed is:

1. A method of treating osteoarthritis in patients in need thereof, said method comprising
    administering to said patients an effective amount of an intra-articular formulation consisting of:
        a) glycine,
        b) proline,
        c) a natural or synthetic viscosity-controlling polymer;
        d) lysine,
        e) leucine; and
        f) suitable excipients; and
    treating said osteoarthritis in said patients.

2. The method as claimed in claim 1, wherein osteoarthritis is patellofemoral or femorotibial knee osteoarthritis, hip osteoarthritis and shoulder osteoarthritis.

3. The method as claimed in claim 1, wherein the natural or synthetic viscosity-controlling polymer is selected from hyaluronic acid or a salt thereof, polyvinylpyrrolidone and cellulose derivatives.

4. The method as claimed in claim 3, wherein the natural or synthetic viscosity-controlling polymer is hyaluronic acid or a salt thereof.

5. The method as claimed in claim 1, wherein the amino acids are in L form.

6. The method as claimed in claim 1, wherein said formulation is in the form of powders for reconstitution or viscous solutions in biocompatible solvents.

7. A method of treating osteoarthritis in patients in need thereof, said method comprising
    administering to said patients an effective amount of an intra-articular formulation consisting of
    the following ranges by weight:
        a) 25 to 500 mg of glycine,
        b) 40 to 300 mg of proline,
        c) 5 to 50 mg of hyaluronic acid or a salt thereof,
        d) 5 to 100 mg of lysine,
        e) 5 to 50 mg of leucine; and
        f) suitable excipients.

* * * * *